(12) United States Patent
Nishiuchi et al.

(10) Patent No.: US 7,569,360 B2
(45) Date of Patent: Aug. 4, 2009

(54) γ-GLUTAMYLCYSTEINE PRODUCING YEAST

(75) Inventors: Hiroaki Nishiuchi, Kawasaki (JP); Reiko Sugimoto, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/853,183

(22) Filed: May 26, 2004

(65) Prior Publication Data

US 2005/0196836 A1 Sep. 8, 2005

Related U.S. Application Data

(63) Continuation of application No. PCT/JP02/12201, filed on Nov. 21, 2002.

(30) Foreign Application Priority Data

Nov. 26, 2001 (JP) ............................. 2001-359782

(51) Int. Cl.
*C12P 21/06* (2006.01)
*C12N 1/16* (2006.01)
*C12N 1/18* (2006.01)

(52) U.S. Cl. .............. 435/68.1; 435/254.2; 435/254.21; 426/7

(58) Field of Classification Search ........................ None
See application file for complete search history.

(56) References Cited

U.S. PATENT DOCUMENTS 5,206,220 A * 4/1993 Hilton .......................... 514/19

FOREIGN PATENT DOCUMENTS

| EP | 1 142 493 A1 | 10/2001 |
|---|---|---|
| EP | 1 201 747 A1 | 5/2002 |
| JP | 6-70752 | 3/1994 |
| WO | WO 00/30474 | 6/2000 |

OTHER PUBLICATIONS

Al-Lahham et al. Yeast, 1999; 15:385-96.*
Polekhina et al. 1999; EMBO J. 18 :3204-13.*
Wang et al. Biochem. J. 1997; 322:241-44.*
Y. Ohtake, et al., Agric. Bio. Chem., vol. 54, No. 12, pp. 3145-3150, "Insolation and Characterization of Glutathione Biosynthesis-Deficient Mutants in *Saccharomyces cerevisiae*", 1990.
C. M. Grant, et al., Molecular Biology of the Cell., vol. 8, pp. 1699-1707, "Glutathione Synthetase is Dispensable for Growth Under Both Normal and Oxidative Stress Conditions in the Yeast *Saccharomyces cerevisiae* Due to an Accumulation of the Dipeptide γ-Glutamylcysteine", Sep. 1997.
Y. Inoue, et al., Biochimica et Biophysica Acta., vol. 1395, p. 315-320, "Molecular Identification of Glutathione Synthetase (GSH2) Gene From *Saccharomyces cerevisiae*", 1998.
Y. Inoue, et al., "Molecular Identification of Glutathione Synthetase (GSH2) Gene From *Saccharomyces cerevisiae*", Biochimica et Biophysica Acta, vol. 135, No. 3, Feb. 11, 1998,pp. 315-320, XP-002945457.
XP-002320495, Database accession No. Y13804.1, EMBL database, Aug. 2001.
XP-002320496, Database accession No. Q08220 Uniprot Database, May 2005.

* cited by examiner

*Primary Examiner*—Celine X Qian
*Assistant Examiner*—Jennifer Dunston
(74) *Attorney, Agent, or Firm*—Oblon, Spivak, McClelland, Maier & Neustadt, P.C.

(57) ABSTRACT

A yeast which harbors a mutant glutathione synthetase having one or both of mutations selected from the group consisting of a mutation to replace a threonine residue at the position 47 with an isoleucine residue and a mutation to replace a glycine residue at the 387-position with an aspartic acid residue and produces γ-glutamylcysteine. The yeast is cultured under suitable conditions, the resultant culture or fractionation product thereof or the resultant culture or fractionation product thereof that had been heat-treated is mixed with food or beverage materials and processed into foods or beverage to produce γ-glutamylcysteine- or cysteine-containing foods or beverage.

13 Claims, 3 Drawing Sheets

γ-GLUTAMYLCYSTEINE PRODUCING YEAST

CROSS-REFERENCE TO RELATED APPLICATIONS

The present application is a continuation of PCT/JP02/12201 filed on Nov. 21, 2002, which claims priority to JP 2001-359782, filed on Nov. 26, 2001.

TECHNICAL FIELD

The present invention relates to a yeast that has a mutant glutathione synthetase with a reduced activity and to a food utilizing cells of the yeast. γ-glutamylcysteine and cysteine produced therefrom are useful in the field of foods.

BACKGROUND ART

Cysteine is used for the purpose of enhancing the flavor of foods and the like. Known production methods of cysteine include a protein decomposition method and a semi-synthetic method. The methods that are currently used in the main are the proteolysys method and the semisynthetic method. Although natural food materials having high cysteine contents have been demanded for the purpose of using them to enhance the flavor of foods, such natural food materials have little been known. On the other hand, it has been reported that heat- or enzyme-treatment of yeast extracts containing γ-glutamylcysteine may give rise to food materials having high cysteine contents (WO 00/30474).

γ-glutamylcysteine is synthesized from cysteine and glutamic acid as substrates by the function of γ-glutamylcysteine synthetase. On the other hand, glutathione is synthesized from γ-glutamylcysteine and glycine as substrates by the function of glutathione synthetase. Therefore, as a method of breeding a yeast that accumulates γ-glutamylcysteine in high contents, there may be proposed disruption of a gene that encodes glutathione synthetase. Yeasts whose genes that encode glutathione synthetase have been disrupted are reported in WO 00/30474; Otake et al., Agri. Biol. Chem., 54(12), 3145-3150, 1990; Chris et al., Molecular Biology of the Cell., 8, 1699-1707, 1997; Inoue et al., Biochimica et Biophysica Acta, 1395(1998) 315-320.

However, each of the above-mentioned yeasts has a defect that their growth rates are decreased to a large extent. Further, Otake, et al. reported that the yeast whose gene encoding glutathione synthetase has been disrupted shows a bad growth under a culture in a medium containing no glutathione in comparison with a culture in a medium containing glutathione (Otake et al., Agri. Biol. Chem., 54(12), 3145-3150, 1990). However, since media containing glutathione in abundance are generally expensive and glutathione itself is also expensive, such media are not preferable for industrial use. On the other hand, it would be also inappropriate to culture the above-mentioned yeasts at high densities in inexpensive media containing insufficient amounts of glutathione for use on an industrial level.

DISCLOSURE OF THE INVENTION

In the above-mentioned technical background, an object of the present invention is to provide a yeast which harbors a mutant glutathione synthetase with a reduced activity and produces γ-glutamylcysteine and a γ-glutamylcysteine-containing food utilizing the yeast.

As a result of extensive studies in order to achieve the above-mentioned object, the inventors of the present invention have found that a mutant glutathione synthetase having a specified mutation has a moderate glutathione synthetase activity suitable for the accumulation of γ-glutamylcysteine and for the growth of the yeast and that the yeast harboring the mutant enzyme accumulates γ-glutamylcysteine, thereby achieving the present invention.

That is, the present invention provides the following.

(1) A yeast which harbors a mutant glutathione synthetase having at least one or both mutation selected from the group consisting of a mutation to replace a threonine residue at the position 47 with an isoleucine residue and a mutation to replace a glycine residue at the position 387 with an aspartic acid residue, and which produces γ-glutamylcysteine.

(2) The yeast according to (1), in which the yeast further has a mutation to replace a proline residue at the position 54 with a leucine residue.

(3) The yeast according to (2), in which the mutant glutathione synthetase has the mutation to replace the threonine residue at the position 47 with an isoleucine residue and the mutation to replace the proline residue at the position 54 with a leucine residue.

(4) The yeast according to (2), in which the mutant glutathione synthetase has the mutation to replace the glycine residue at the position 387 with an aspartic acid residue and the mutation to replace the proline residue at the position 54 with a leucine residue.

(5) The yeast according to any one of (1) to (4), in which a glutathione synthetase free of the mutation has the amino acid sequence of SEQ ID NO:2.

(6) The yeast according to any one of (1) to (5), in which the yeast belongs to the genus *Saccharomyces*.

(7) A food or beverage comprising a culture obtained by culturing the yeast according to any one of (1) to (6) under a suitable condition, or a fractionation product of the above-mentioned culture containing γ-glutamylcysteine, or the culture or fractionation product in which cysteine has been produced by a heat treatment.

(8) The food or beverage according to (7), in which the food or beverage is an alcoholic beverage, a bread food, or a fermented food flavoring material.

(9) The yeast extract produced by using a culture obtained by culturing a yeast according to any one of (1) to (6) under a suitable condition.

(10) A method of producing food or beverage which contains γ-glutamylcysteine or cysteine, comprising the steps of culturing a yeast according to any one of (1) to (6) under a suitable condition, mixing the obtained culture or fractionation product thereof, or the culture or fractionation product thereof subjected to heat treatment with a food or beverage raw material, and processing the mixture into a food or beverage.

Hereinafter, the present invention will be described in detail.

The yeast of the present invention is a yeast which harbors a mutant glutathione synthetase having one or both of the following mutations and produces γ-glutamylcysteine.

(1) Mutation to substitute the threonine residue at the position 47 by an isoleucine residue (hereinafter, also referred to as "T47I-type" mutation); and (2) Mutation to substitute the glycine residue at the position 387 by an aspartic acid residue (hereinafter, also referred to as "G387D-type" mutation).

In the present invention, "harboring a mutant glutathione synthetase" presupposes harboring substantially no wild-type glutathione synthetase.

Also, in the present invention, "producing γ-glutamylcysteine" means accumulating γ-glutamylcysteine in the microbial cells in a larger amount than a wild-type yeast strain does. Preferably, the yeast of the present invention when cultured in an SD medium contains 1.0% by weight or more, more preferably 1.1% by weight or more, of γ-glutamylcysteine in its logarithmic growth phase. Furthermore, the yeast of the present invention when cultured in an SD medium contains glutathione in a range of 0.0001% to 0.1% by weight, preferably in a range of 0.001% to 0.006% by weight, in its logarithmic growth phase. The term "logarithmic growth phase" as used herein refers to a phase in which the number of yeast cells during the culture increases logarithmically with respect to culture time.

The above-mentioned positions of mutation of glutathione synthetase and of optional mutations described hereinbelow are determined with reference to the reported amino acid sequence encoded by a glutathione synthetase gene (GSH2) of *Saccharomyces cerevisiae* (Inoue et al., Biochim. Biophys. Acta, 1395 (1998) 315-320, GenBank accession Y13804) (shown in SEQ ID NO:2 in the sequence listing). The nucleotide sequence of the same gene is shown in SEQ ID NO:1.

For example, in the case where the mutant glutathione synthetase harbored by the yeast of the present invention has a deletion of one amino acid residue at the N-terminal portion as compared with the reference sequence, the above-mentioned positions 47 and 387 correspond to the 46th and 386th amino acid residues, respectively, from the N-terminal of the mutant glutathione synthetase.

The yeast of the present invention may further have one or both of the following mutations in addition to the above-mentioned mutation.

(3) Mutation to substitute the proline residue at the position 54 by a leucine residue (hereinafter, also referred to as "P54L-type" mutation).

A preferred embodiment of the mutant glutathione synthetase harbored by the yeast of the present invention is as follows.

(i) A glutathione synthetase having a T47I-type mutation and a P54L-type mutation.
(ii) A glutathione synthetase having a G387D-type mutation and a P54L-type mutation.

Furthermore, the above-mentioned mutant glutathione synthetase is preferably one in which glutathione synthetase free of the mutation has amino acid sequence shown in SEQ ID NO:2.

Since the mutant glutathione synthetase having the above-mentioned mutation has a reduced activity as compared with the wild-type glutathione synthetase, the yeast which harbors the mutant enzyme produces γ-glutamylcysteine. Furthermore, since the yeast which harbors the above-mentioned mutant glutathione synthetase retains a reduced glutathione synthetase activity, it can also grow well in a medium containing no glutathione.

The yeast of the present invention is not particularly limited so far as it can produce γ-glutamylcysteine. Specifically, it includes yeasts belonging to the genera *Saccharomyces* such as *Saccharomyces cerevisiae*, *Schizosaccharomyces* such as *Schizosaccharomyces pombe*, and the like. It is preferred that the yeast of the present invention has dipoloidy or more polyploidy in consideration of good growth. The yeast having diploidy or more polyploidy can be obtained by mating the monoploid yeast used in breeding the yeast harboring the above-mentioned mutant glutathione synthetase with a monoploid of a wild-type glutathione synthetase-harboring strain and selecting a strain which harbors the mutant glutathione synthetase and produces γ-glutamylcysteine from the obtained diploid yeasts. Similarly, yeasts having triploidy or more polyploidy can be obtained.

The yeast of the present invention can be created by gene substitution using, for example, DNA encoding the glutathione synthetase having the above-mentioned mutation. The yeast of the present invention can also be obtained by subjecting the wild-type yeast to an ordinary mutation treatment such as UV irradiation, or a treatment with a mutagen such as N-methyl-N-nitrosoguanidine (NTG), ethyl methanesulfonate (EMS), nitrous acid, or acridine. It can be confirmed that the obtained mutant has the objective mutation by, for example, a PCR method or the like.

The above-mentioned gene substitution can be performed as follows. That is, a yeast is transformed with a recombinant DNA containing a nucleotide sequence that encodes the glutathione synthetase having introduced therein the objective mutation to cause recombination between the mutant glutathione synthetase gene and the glutathione synthetase gene on the chromosome. On this occasion, a marker gene inserted in the recombinant DNA depending on the characteristic such as auxotrophy of the host makes the manipulation easy. Furthermore, making the above-mentioned recombinant DNA linear, by cleavage with a restriction enzyme or the like and in addition removal of a replication control region that functions in yeasts from the recombinant DNA can efficiently give rise to a strain in which the recombinant DNA is incorporated into the chromosome.

The strain in which the recombinant DNA has been incorporated into the chromosome in the above-mentioned manner undergoes recombination with a glutathione synthetase gene sequence inherently existing on the chromosome, so that the two fused genes, i.e., the wild-type glutathione synthetase gene and the mutant glutathione synthetase gene, are inserted into the chromosome so that the other parts of the recombinant DNA (vector segment and marker gene) should be present between the two fusion genes. Therefore, in this state, the wild-type glutathione synthetase gene functions.

Next, to leave only the mutant glutathione synthetase gene on the chromosomal DNA, one copy of glutathione synthetase gene together with the vector segment (including also the marker gene) is eliminated from the chromosomal DNA by recombination of the two glutathione synthetase genes. On this occasion, there are two cases. In one case, the wild-type glutathione synthetase gene is left on the chromosomal DNA and the mutant glutathione synthetase gene is excised therefrom. In another case, on the contrary, the mutant glutathione synthetase gene is left on the chromosomal DNA and the wild-type glutathione synthetase gene is excised. In both cases, the marker gene is eliminated so that the occurrence of a second recombination can be confirmed by phenotype corresponding to the marker gene. The objective gene-substituted strain can be selected by amplifying the glutathione synthetase gene by a PCR method and examining its structure.

The mutant glutathione synthetase gene used in gene substitution may be one that encodes full-length glutathione synthetase but may also be a gene fragment that encodes a part of the enzyme so far as it includes the mutation site. Also, when a gene fragment is used, gene substitution performed in the same manner as described above will result in introduction of the objective mutation into the wild-type glutathione synthetase gene on the chromosomal DNA.

In the case where the glutathione synthetase gene on the chromosomal DNA and the mutant glutathione synthetase gene contemplated to be introduced have low homology to each other to such an extent that a gene substitution method cannot be applied thereto, the glutathione synthetase gene on the chromosomal gene may be disrupted and followed by harboring the mutant glutathione synthetase gene on a plasmid or a chromosomal DNA.

The mutant glutathione synthetase gene having the desired mutation can be obtained by a site-specific mutation using synthetic oligonucleotides. The nucleotide sequence of the glutathione synthetase gene of Saccharomyces cerevisiae has been reported (Inoue et al., Biochim. Biophys. Acta, 1395 (1998) 315-320, GenBank accession Y13804, SEQ ID NO:1), and the gene can be obtained from the chromosomal DNA of Saccharomyces cerevisiae by a PCR method in which an oligonucleotide prepared based on the nucleotide sequence is used as primers.

For the transformation of yeasts, those methods conventionally used in the transformation of yeasts, such as a protoplast method, a KU method, a KUR method, an electroporation method, or the like may be employed. Furthermore, manipulation procedures such as spore formation of yeast and separation of monoploid yeast, and the like are described in "Chemistry and Organisms, Experimental Line 31, Experimental Techniques on Yeasts" First Edition, Hirokawa Shoten; "Bio Manual Series 10, Gene Experimental Methods with Yeasts", First Edition, Youdosha, and the like.

The yeast of the present invention may be enhanced in γ-glutamylcysteine activity in addition to harboring a mutant glutathione synthetase.

The yeast of the present invention produces γ-glutamylcysteine in a certain amount or more and grows well in a medium used on an industrial level which contains no glutathione, so that it is excellent in ability of producing γ-glutamylcysteine per unit time.

The culture obtained by culturing the γ-glutamylcysteine-producing yeast obtained as described above under suitable conditions contains γ-glutamylcysteine. Such a culture or fractionation product thereof contains γ-glutamylcysteine. The culture may be a culture broth containing yeast cells or may be yeast cells collected therefrom, disrupted cells or cell extracts (yeast extracts). It is also recommendable to obtain a fractionation product containing γ-glutamylcysteine from the cell fragments or yeast extracts.

Heating the above-mentioned culture containing γ-glutamylcysteine or a fractionation product thereof can release cysteine from γ-glutamylcysteine.

The medium to be used for culture is not particularly limited so far as it allows the yeast of the present invention to grow well and efficiently produce γ-glutamylcysteine. For the yeast of the present invention, due to its ability of growing well on a medium containing no glutathione, media usually used on an industrial scale can be used. Note that, necessary nutrients may be added to the medium as necessary depending on the characteristics of the yeast used.

Culture conditions and preparation of yeast extracts and the like may be performed in the same manner as usual yeast culture and preparation of yeast extracts and the like are performed. The yeast extracts may be those obtained by treating hot water extracts of yeast cells or those obtained by treating digested yeast cells.

The above-mentioned culture or fractionation product thereof that contains γ-glutamylcysteine or cysteine can be used for the production of foods and beverage. The foods and beverage include alcoholic beverage, bread foods, and fermented food flavoring materials. Production of cysteine from γ-glutamylcysteine by heat treatment may be performed during the production of foods and beverage or after their production.

The above-mentioned foods and beverage are produced by mixing a culture or a fractionation product thereof containing γ-glutamylcysteine or cysteine with a food or beverage raw material and processing the mixture into a food or beverage. The food and beverage of the present invention can be produced by using the same raw materials as those used for usual foods and beverage and by the same method as that used for usual foods and beverage except that the above-mentioned culture or fractionation product is used. Such raw materials include, for example, rice, barley, cornstarch, etc. for alcoholic beverage, wheat flour, sugar, table salt, butter, fermentation yeast, etc. for bread foods, and soybean and wheat, etc. for fermented food flavoring materials.

DESCRIPTION OF PREFERRED EMBODIMENTS

Figure 1:
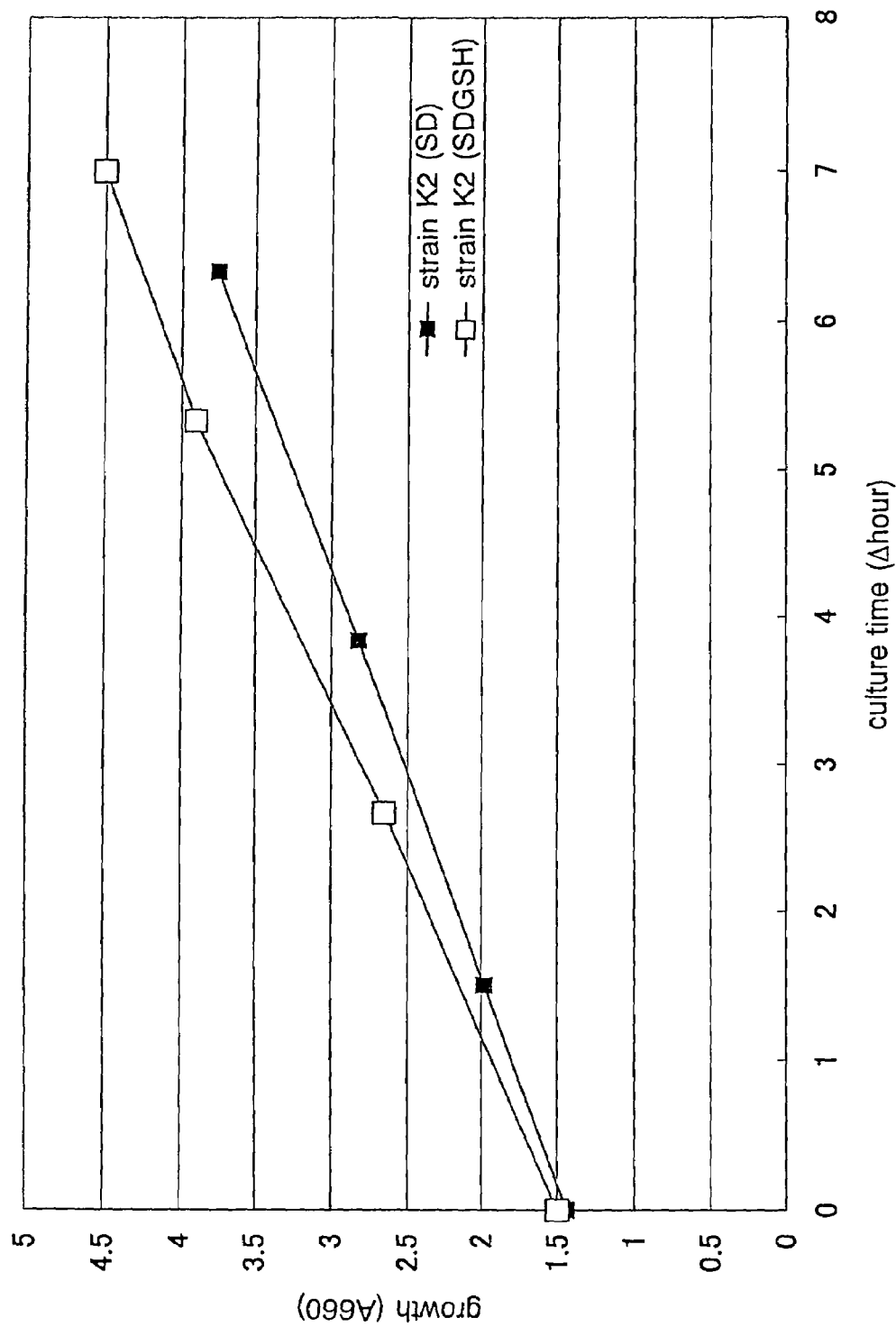
FIG. 1 is a diagram showing the growth of K2 strain in an SD medium or an SD medium containing 1-mM glutathione (SDGSH), with each medium containing a necessary amount of uracil.

Hereinafter, the present invention will be described in detail with reference to Examples.

The compositions of the media used in the Examples are as follows. Note that agar media contain 2% of purified agar.

| [YPD medium composition] | |
|---|---|
| Glucose | 2% |
| Peptone | 1% |
| Yeast extract | 0.5% |
| (pH 5.0) | |
| [SD medium composition] | |
| Glucose | 2% |
| Nitrogen Base | 1-fold concentration |

(10-Fold concentration Nitrogen Base is a mixture of 1.7 g of Bacto Yeast Nitrogen Base w/o Amino Acid and Ammonium Sulfate (Difco Laboratories, Inc.) and 5 g of ammonium sulfate dissolved in 100 ml of sterilized water, adjusted to about pH 5.2 and sterilized by filtration through a filter).

[Composition of SDFOA Medium]

SD media containing 50 mg/l of uracil and 1 g/l of 5-fluoroorotic acid hydrate in final concentrations.

COMPARATIVE EXAMPLE 1

Breeding of a Yeast in which the Gene Encoding Glutathione Synthetase was Disrupted Commercially available Saccharomyces cerevisiae used for foods was allowed to form spores to obtain a monoploid bread yeast, strain S (MATα). Furthermore, an uracil auxotrophic strain S2 was obtained from the strain S by using an SDFOA agar medium containing uracil. From the strain S2 was obtained a yeast strain K1 in which the glutathione synthetase gene (GSH2) was disrupted by the method described in WO 00/30474 A.

EXAMPLE 1

Breeding of a Yeast Having a Mutant Glutathione Synthetase

<1> Preparation of a Cassette for the Substitution of a Reduced-type Glutathione Synthetase Gene (1) Preparation of a Cassette for the Substitution of a G387D Type Glutathione Synthetase Gene Using primer F1 (CATAAAACAACTGAAGCGT-TAGCTC (SEQ ID NO:3)) and R1 (CAGGCCAAA-GATTTTCAGTACGAGC (SEQ ID NO:4)) and Pyrobest DNA Polymerase (Takara Shuzo) under the conditions indicated by the manufacturer was amplified a region encoding a segment from the midstream of the open reading frame (ORF) of the glutathione synthetase gene of S2 strain to about 40 bp downstream of the ORF by a polymerase chain reaction (PCR) method.

The gene fragment amplified as described above was purified and an enzymatic reaction was performed at 72° C. for 10 minutes under the following conditions to add a nucleotide A to each of the termini.

| (Reaction mixture composition) | |
|---|---|
| Gene fragment solution | 5 µl |
| 10 × PCR buffer (MgCl$_2$ free) | 5 µl |
| 25 mM MgCl$_2$ | 3 µl |
| 2.5 mM dATP | 5 µl |
| Taq DNA polymerase (Takara Shuzo) | 0.5 µl |
| Purified water | 31.5 µl |
| Total | 50 µl |

The reaction product described above was ligated to plasmid pGEM-T Easy (Promega Corporation) according to the instruction of the manufacturer to obtain a plasmid GSH2MS41/pGEM.

Next, by site-specific mutation, a codon (GGT) corresponding to the 387th amino acid (Gly) of the glutathione synthetase gene contained in GSH2MS41/pGEM was substituted by an Asp codon (GAT). This operation was performed by using QuikChange™ Site-Directed Mutagenesis Kit (Stratagene) according to the protocol provided by the manufacturer. As the primers were used Primer F2 (CCA-CAGCGGGAAGATGGCGGAAACAATG (SEQ ID NO:5)) and Primer R2 (CATTGTTTCCGCCATCTTCCCGCT-GTGG (SEQ ID NO:6)). Thus, a plasmid GSH2MS41dash/pGEM was prepared.

On the other hand, a plasmid corresponding to the plasmid pYES2 (Invitrogen) from which 2µ ori was removed was prepared. pYES2 was cleaved with restriction enzymes SspI and NheI and the cleaved ends were blunted and then re-circularized to obtain a plasmid pYES2dash. pYES2dash and GSH2MS41dash/pGEM were each cleaved with restriction enzymes SacI and SphI to cleave out a fragment containing URA3 gene from pYES2dash and a glutathione synthetase gene fragment having a mutation from GSH2MS41dash/pGEM, and these were ligated to each other. Thus a plasmid GSH2MS41dash/pYES2dash was prepared. GSH2MS41dash/pYES2dash was digested with a restriction enzyme MunI to obtain a cassette 1.

(2) Preparation of a Cassette for the Substitution of a T47I-Type Glutathione Synthetase Gene Using primer F3 (CTAATATGGATGTCGGCAAC-CCAAG (SEQ ID NO:7, corresponding to a region about 700 base pairs upsteam from the ORF of a GSH2 gene that encodes the glutathione synthetase)) and primer R3 (CCA-CAGCTTTGGCCAATGCCTTAG (SEQ ID NO:8)) and Pyrobest DNA Polymerase (Takara Shuzo) under the conditions indicated by the manufacturer, a fragment including the glutathione synthetase gene of S2 strain was amplified by a polymerase chain reaction (PCR) method.

The gene fragment amplified as described above was purified and an enzymatic reaction was performed at 72° C. for 10 minutes under the same conditions as that described above to add nucleotide A to each of the termini.

The reaction product obtained as described above was ligated to plasmid pGEM-T Easy (Promega) according to instructions provided by the manufacturer to obtain a plasmid GSH2FD63/pGEM.

Next, a codon (ACT) corresponding to the 47th amino acid, Thr, of the glutathione synthetase gene contained in GSH2FD63/pGEM was substituted by an Ile codon (ATT). This operation was performed by using QuikChange™ Site-Directed Mutagenesis Kit (Stratagene) according to the protocol provided by the manufacturer. As the primers, primer F4 (CGGTGTCACCAGTAATTATCTATCCAACCCC (SEQ ID NO:9)) and primer R4 (GGGGTTGGATAGATAAT-TACTGGTGACACCG (SEQ ID NO:10)) were used. Thus, a plasmid GSH2FD63dash/pGEM was prepared.

pYES2dash and GSH2FD63dash/pGEM were each cleaved with restriction enzymes SacI and SphI to cleave out a fragment containing URA3 gene from pYES2dash and a glutathione synthetase gene fragment having a mutation from GSH2FD63dash/pGEM, and these were ligated to each other. Thus a plasmid GSH2FD63dash/pYES2dash was prepared. GSH2FD63dash/pYES2dash was cleaved with a restriction enzyme to obtain a cassette 2.

<2> Breeding of a Yeast Harboring a Reduced-type Glutathione Synthetase (1) Breeding of a Yeast Harboring a G387D-type Glutathione Synthetase Using the cassette 1 prepared as described above, gene substitution of the glutathione synthetase gene of S2 strain was performed. After preculturing the S2 strain, the culture was subcultured in 50 ml of YPD medium and cultured until the logarithmic growth phase. The cultured cells were suspended in 1M sorbitol and the cassette 1 was mixed to perform transformation by electroporation. The transformant strain was cultured on an SD plate containing 1 mM glutathione and a strain that grows thereon was selected. After confirming incorporation of the cassette 1 to the objective site on the chromosome by PCR, the obtained strain was named K2 intermediate. The K2 intermediate was cultured and spread on an SDFOA agar medium. Then, a yeast strain K2 in which the glutathione synthetase was substituted by G387D-type was obtained from the strains that grew.

The results of comparison with the reported nucleotide sequence of the glutathione synthetase gene of *Saccharomyces cerevisiae* (Inoue et al., Biochim. Biophys. Acta, 1395 (1998) 315-320, GenBank accession Y13804) indicate that the mutant glutathione synthetase gene of the K2 strain has substitution of the codon of proline residue (CCT) at the position 54 by the codon of leucine residue (CCT) in addition to the above-mentioned G387D-type mutation.

(2) Breeding of a Yeast Harboring a T47I-type Glutathione Synthetase

Using the cassette 2 prepared as described above, gene substitution of the glutathione synthetase gene of S2 strain was performed. After preculturing the S2 strain, the culture was subcultured in 50 ml of YPD medium and cultured until the logarithmic growth phase. The cultured cells were suspended in 1M sorbitol and the cassette 2 was mixed to perform transformation by electroporation. The transformant strain was cultured on an SD plate containing 1 mM glutathione and a strain that grows thereon was selected. The incorporation of the cassette 2 at the objective position on the chromosome was confirmed by a PCR method, and the obtained strain was named K3 intermediate. The K3 intermediate was cultured and spread on an SDFOA agar medium. The transformant that grew was spread on an SD agar medium and the strains that grew were selected to obtain a K3 intermediate strain into which the gene substitution cassette 2 was introduced. The K3 intermediate strain was cultured and spread on an SDFOA agar medium. Then, a yeast strain K3 in which the glutathione synthetase gene was substituted by the T47I -type was obtained from the strains that grew.

The results of comparison with the reported nucleotide sequence of the glutathione synthetase gene of *Saccharomyces cerevisiae* (Inoue et al., Biochim. Biophys. Acta, 1395 (1998) 315-320, GenBank accession Y13804) indicate that the mutant glutathione synthetase gene of the K3 strain has substitution of the codon of proline residue (CCT) at the position 54 by the codon of leucine residue (CCT) in addition to the above-mentioned T47I-type mutation.

(3) Preparation of a Diploid Yeast

Monoploid yeast (MATα) having a G387D-type mutant glutathione synthetase (K2 strain) was mated with a monoploid yeast (MATa) by a conventional method to obtain a diploid yeast. The diploid yeast was made to form spores by a conventional method to obtain a monoploid yeast (MATa) having the G387D-type mutant glutathione synthetase. Then, the monoploid yeast (MATα) having the G387D-type mutant glutathione synthetase and the monoploid yeast (MATα) having the G387D-type mutant glutathione synthetase were mated to each other to obtain a diploid yeast strain Z1 having the G387D-type mutant glutathione synthetase in the form of a homozygote. A diploid yeast strain Z2 having the T47I-type mutant glutathione synthetase was also obtained in a similar manner. It was confirmed that the strains Z1 and Z2 accumulated γ-glutamylcysteine in amounts of 1% or more per dry yeast cell.

<3> Studies on the Growth of a Yeast Having the Mutant Glutathione Synthetase and its Productivity of γ-Glutamylcysteine (1) Growth of Strains K2 and K3

Figure 2:
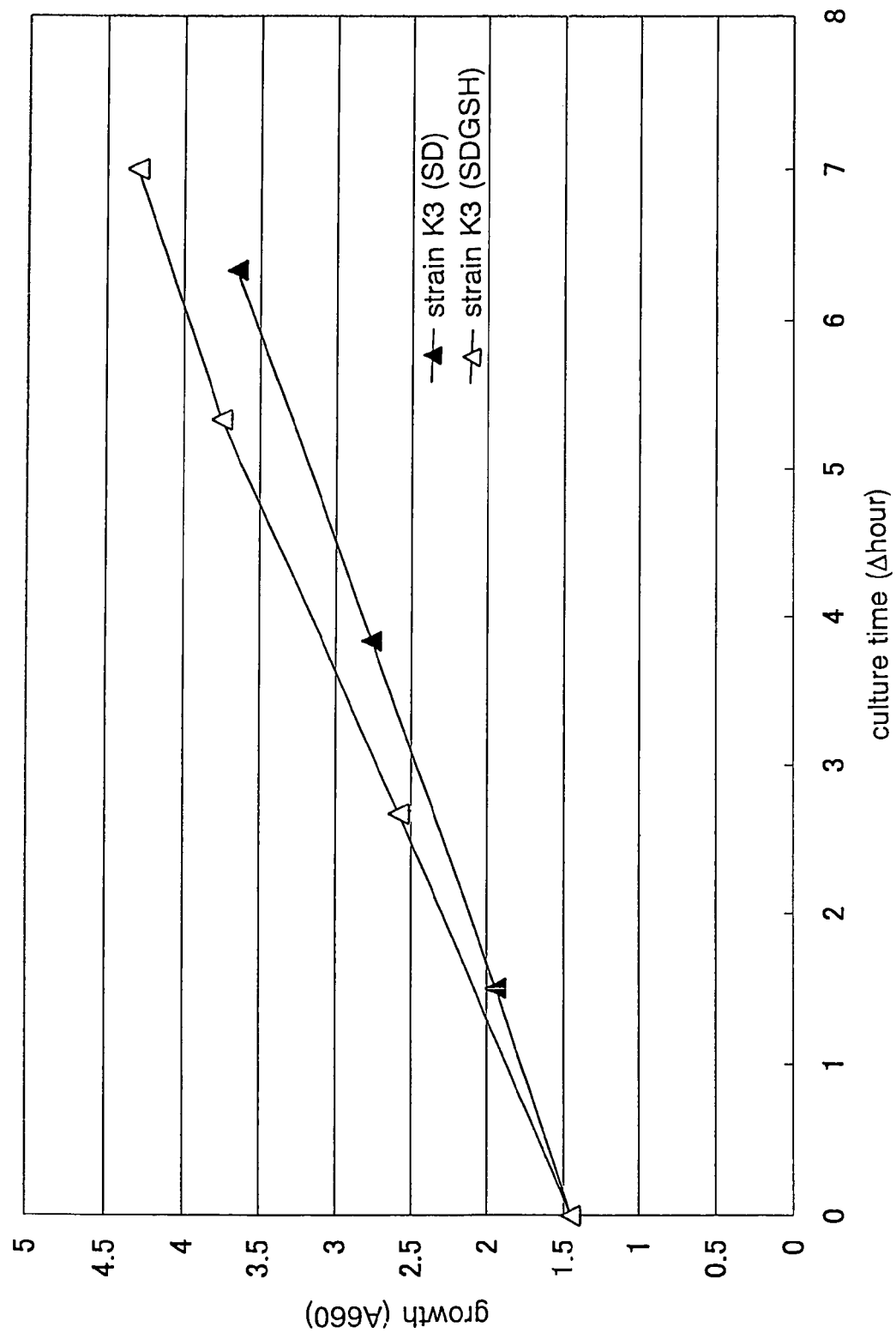
FIG. 2 is a diagram showing the growth of K3 strain in an SD medium or an SD medium containing 1-mM glutathione (SDGSH), with each medium containing a necessary amount of uracil.
Figure 3:
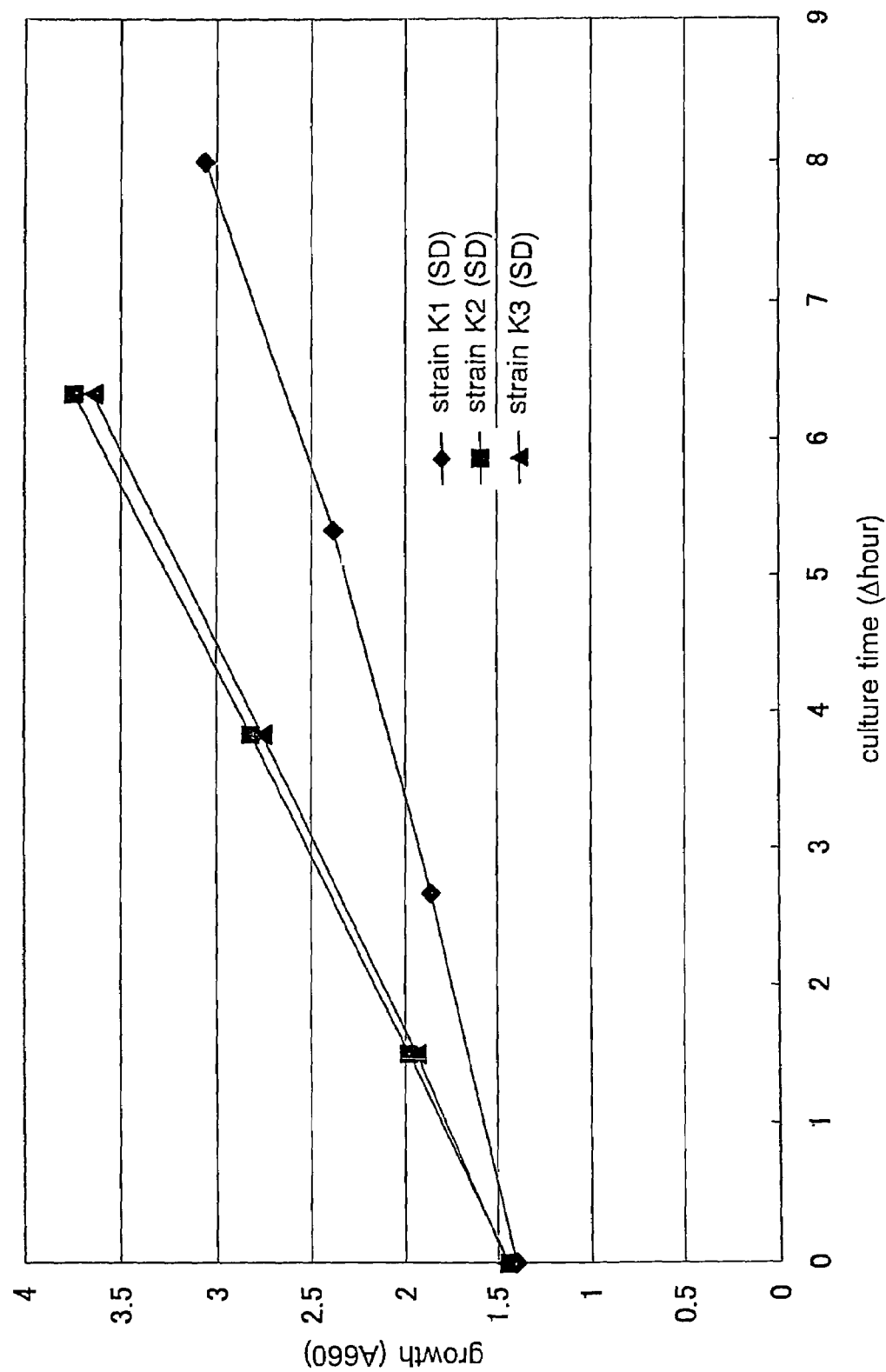
FIG. 3 is a diagram showing the growths of K1, K2 and K3 strains, respectively, in SD media (containing necessary amounts of uracil).

The strains K1, K2 and K3 were cultured in SD media (containing necessary amounts of uracil) or SD media containing 1 mM of glutathione (containing necessary amounts of uracil). Measurement of their growth was started at the time when the growth of the yeasts reached a logarithmic growth phase and the absorbance at 660 nm became 1.4 or more. The results obtained are shown in FIGS. 1 to 3.

The specific growth rate (degree of growth per 1 hour) of the strain K2 on a medium containing glutathione was 1.171 while its specific growth rate on a medium containing no glutathione was 1.161. The specific growth rate of the strain K3 was 1.169 on the medium containing glutathione and 1.156 on the medium containing no glutathione. As will be apparent from FIGS. 1 to 3 and from the specific growth rates, the strains K2 and K3 also grew well on media containing no glutathione and hence is more suitable for culture on an industrial level than the strain of which the glutathione synthetase gene has been destructed. Therefore, yeasts having a G387D-type or T47I-type glutathione synthetase can be advantageously used for cultures on an industrial level on a medium without glutathione or with a small amount of glutathione.

(2) Productivity of γ-Glutamylcysteine of Strains K2 and K3

The strains K1, K2 and K3 were cultured in SD media (containing necessary amounts of uracil). Measurements of their growth and accumulation amount of γ-glutamylcysteine were started at the time when the growth of the yeasts reached a logarithmic growth phase and the absorbance at 660 nm became 1.4 or more. The specific growth rates of the strains were 1.104, 1.161 and 1.156, respectively. The strains K2 and K3 accumulated glutathione in amounts of 0.001% or more and 0.006% or less per dry yeast cell. The γ-glutamylcysteine accumulation amount of each strain per dry yeast cell in a logarithmic growth phase was as follows.

TABLE 1

| | Culture time after start of measurement | γ-glutamylcysteine (%) |
| --- | --- | --- |
| strain K1 | about 2.6 hours later | 1.750 |
| strain K1 | about 5.3 hours later | 1.747 |
| strain K2 | about 1.5 hours later | 1.121 |
| strain K2 | about 3.8 hours later | 1.125 |
| strain K3 | about 1.5 hours later | 1.118 |
| strain K3 | about 3.8 hours later | 1.120 |

Next, the productivity of γ-glutamylcysteine per unit time was measured. The productivity of γ-glutamylcysteine per unit time was measured by an increase in the amount of γ-glutamylcysteine contained in a Sakaguchi flask per unit time when each strain was cultured therein in 50 ml of SD medium (containing a necessary amount of uracil). This value is controlled by the γ-glutamylcysteine accumulation amount per dry cell and the growth rate of the yeast. The values were 0.116 mg/hour for the strain K1, 0.130 mg/hour for the strain K2, and 0.127 mg/hour for the strain K3.

A yeast containing γ-glutamylcysteine in an amount of 1% by weight or more per dry yeast cell and yeast extracts therefrom have been reported to be usable for enhancing the flavor of foods (WO 00/30474). Therefore, the strains K2 and K3, which have greater specific growth rates than that of the strain K1, are advantageous for producing a yeast containing 1% or more of γ-glutamylcysteine per dry yeast cell and yeast extracts therefrom. In addition, the strains K2 and K3 are higher in productivity of γ-glutamylcysteine per unit time than that of the strain K1. Furthermore, since the strains K2 and K3 contain 0.001% or more of glutathione, they are suitable for cultures on an industrial level in which no glutathione is contained. From the above viewpoints, the yeast having the G387D-type or T47I type mutant glutathione synthetase can be said to be suitable for the production of yeasts containing γ-glutamylcysteine and yeast extracts therefrom.

(3) Studies on Stability of Subculture of Strains K2 and K3

The strains K2, K3, Z1 and Z2 were cultured on YPD media. These strains were each subcultured ten times and whether or not reverse mutation occurred was examined. The subculture was performed as follows. That is, each strain was inoculated into a test tube containing 4 ml of a YPD liquid medium and cultured with shaking at 30° C. After sufficient growth, a portion of the culture was subcultured in a test tube containing 4 ml of a YPD liquid medium. This operation was repeated ten times.

Whether or not reverse mutation occurred was confirmed as follows. That is, the yeast cells were collected from the culture broth and the chromosomal DNAs thereof were collected, followed by confirmation of the nucleotide sequences of the mutation points. In addition, presence or absence of growth when cultured at 30° C. on an SD agar medium containing 10-mM methyl glyoxal (containing a necessary amount of uracil) was confirmed. These results demonstrated the stability of subcultures of the strains K2, K3, Z1 and Z2.

(4) Studies on P54L Mutation

The influence of P54L mutation on the mutant glutathione synthetase was studied.

A plasmid containing a glutathione synthetase gene having the T47I-type or the G387D-type mutation alone was prepared. As the plasmid containing a glutathione synthetase gene, pEGSH2 was used. This plasmid was prepared by the method described in a literature (Inoue, et al., Biochim. Biophys. Acta, 1395 (1998) 315-320).

First, the codon (ACT) corresponding to 47th amino acid, Thr, of the glutathione synthetase gene of plasmid pEGSH2 was substituted by a codon (ATT) of Ile. This operation was performed using Quik Change™ Site-Directed Mutagenesis Kit (Stratagene) in accordance with the manufacturer's protocol. As the primers, primer F4 (CGGTGTCACCAGTAATTATCTATCCAACCCC (SEQ ID NO:9)) and primer R4 (GGGGTTGGATAGATAATTACTGGTGACACCG (SEQ ID NO:10)) were used. Thus, plasmid pEGSH2-T47I was constructed.

Next, the codon (GGT) corresponding to 387th amino acid, Gly, of the glutathione synthetase gene of plasmid pEGSH2 was substituted by a codon (GAT) of Asp. This operation was performed using Quik Change™ Site-Directed Mutagenesis Kit (Stratagene) in accordance with the manufacturer's protocol. As the primers, primer F2 (CCACAGCGGGAAGATGGCGGAAACAATG (SEQ ID NO:5)) and primer R2 (CATTGTTTCCGCCATCTTCCCGCTGTGG (SEQ ID NO:6)) were used. Thus, plasmid pEGSH2-G387D was constructed.

On the other hand, the strain K1dash that shows uracil requirement was obtained from the strain K1 as follows. That is, the strain K1 was cultured in a YPD medium at 30° C. for 80 hours and the culture was spread on an SDFOA plate. From among the yeasts that grew on the SDFOA plate was selected a yeast strain, K1dash, that showed uracil requirement and whose glutathione synthetase had been destructed.

The strain K1dash obtained as described above was transformed with the above-mentioned plasmids pEGSH2, pEGSH2-T47I, and pEGSH2-G387D to obtain pEGSH2/K1dash, pEGSH2-T47I/K1dash, and pEGSH2-G387D/K1dash strains, respectively. The transformation of K1dash strains with each plasmid was performed as follows. That is, after preculturing the K1dash strain, the culture was subcultured in 50 ml of YPD medium and cultured until a logarithmic growth phase was reached. The cultured cells were suspended in 1 M sorbitol, the objective plasmid was mixed, and transformation was performed by electroporation. The transformants were cultured on an SD agar medium containing 1 mM of glutathione and strains that grew were selected.

The strains pEGSH2/K1dash, pEGSH2-T47I/K1dash, and pEGSH2-G387D/K1dash were cultured with shaking in SD media at 30° C. for 30 hours and cultures were inoculated in SD media in a concentration of 2% and cultured with shaking at 30° C. The amount of glutathione accumulated in cells in the logarithmic growth phase thereof (10 hours after this culture was started) was measured. Glutathione was accumulated in an amount of about 0.80% in the case of the pEGSH2/K1dash strain, and in an amount of 0.001 to 0.006% in the case of the pEGSH2-T47I/K1dash and pEGSH2-G387D/K1dash strains.

The above-mentioned results indicate that yeasts can have a reduced glutathione synthetase activity with the mutations T47I or G387D alone and without the mutation P54L and can contain a slight amount of glutathione in the cells, thereby contributing to high productivity of γ-glutamylcysteine.

INDUSTRIAL APPLICABILITY

According to the present invention, a yeast which harbors a mutant glutathione synthetase with a reduced activity and produces γ-glutamylcysteine is provided. The yeast of the present invention can be used in producing γ-glutamylcysteine-containing foods or cysteine-containing foods.

The invention claimed is:

1. An isolated yeast comprising a mutant glutathione synthetase wherein the corresponding, unmutated wild-type glutathione synthetase consists of the amino acid sequence of SEQ ID NO: 2 and said mutant glutathione synthetase has one or more mutations selected from the group consisting of
   a mutation to replace $Thr_{47}$ in the amino acid sequence of SEQ ID NO: 2 with an isoleucine residue, and
   a mutation to replace $Gly_{387}$ in the amino acid sequence of SEQ ID NO: 2 with an aspartic acid residue,
   wherein said yeast produces γ-glutamylcysteine.

2. The isolated yeast according to claim 1, wherein said mutant glutathione synthetase further comprises a mutation to replace $Pro_{54}$ in the amino acid sequence of SEQ ID NO: 2 with a leucine residue.

3. The isolated yeast according to claim 2, wherein said mutant glutathione synthetase has a mutation to replace $Thr_{47}$ with an isoleucine residue and a mutation to replace $Pro_{54}$ in the amino acid sequence of SEQ ID NO: 2 with a leucine residue.

4. The isolated yeast according to claim 2, wherein said mutant glutathione synthetase has a mutation to replace $Gly_{387}$ with an aspartic acid residue and a mutation to replace $Pro_{54}$ in the amino acid sequence of SEQ ID NO: 2 with a leucine residue.

5. The isolated yeast according to claim 1, wherein the yeast belongs to the genus *Saccharomyces*.

6. The isolated yeast according to claim 1, wherein the yeast belongs to the genus *Schizosaccharomyces*.

7. The isolated yeast according to claim 1, wherein the yeast is diploid or polyploid.

8. The isolated yeast according to claim 1, wherein the yeast is *Saccharomyces cerevisiae*.

9. A method of producing γ-glutamylcysteine comprising culturing a yeast strain according to claim 1 under conditions and for a time suitable to produce γ-glutamylcysteine and recovering said γ-glutamylcysteine.

10. A method of producing food which contains γ-glutamylcysteine or cysteine, comprising
   culturing a yeast strain according to claim 1,
   mixing the culture with a beverage or food raw material, and
   processing the mixture into a food or beverage.

11. The method according to claim 10, wherein said culture is heat-treated.

12. The method according to claim 10, wherein after said culturing said yeast strain is fractionated.

13. The method according to claim 12, wherein the fractionated culture is heat-treated.

* * * * *

SEQUENCE LISTING

```
<160> NUMBER OF SEQ ID NOS: 10

<210> SEQ ID NO 1
<211> LENGTH: 2466
<212> TYPE: DNA
<213> ORGANISM: Saccharomyces cerevisiae
<220> FEATURE:
<221> NAME/KEY: CDS
<222> LOCATION: (1)..(1476)
<223> OTHER INFORMATION:

<400> SEQUENCE: 1 atg gca cac tat cca cct tcc aag gat caa ttg aat gaa ttg atc cag      48
Met Ala His Tyr Pro Pro Ser Lys Asp Gln Leu Asn Glu Leu Ile Gln
1               5                   10                  15 gaa gtt aac caa tgg gct atc act aat gga tta tcc atg tat cct cct      96
Glu Val Asn Gln Trp Ala Ile Thr Asn Gly Leu Ser Met Tyr Pro Pro
            20                  25                  30
```

-continued

| | | |
|---|---|---|
| aaa ttc gag gag aac cca tca aat gca tcg gtg tca cca gta act atc<br>Lys Phe Glu Glu Asn Pro Ser Asn Ala Ser Val Ser Pro Val Thr Ile<br>35                       40                    45 | 144 |
| tat cca acc cca att cct agg aaa tgt ttt gat gag gcc gtt caa ata<br>Tyr Pro Thr Pro Ile Pro Arg Lys Cys Phe Asp Glu Ala Val Gln Ile<br>50                       55                    60 | 192 |
| caa ccg gta ttc aat gaa tta tac gcc cgt att acc caa gat atg gcc<br>Gln Pro Val Phe Asn Glu Leu Tyr Ala Arg Ile Thr Gln Asp Met Ala<br>65                       70                   75                    80 | 240 |
| caa cct gat tct tat tta cat aaa aca act gaa gcg tta gct cta tca<br>Gln Pro Asp Ser Tyr Leu His Lys Thr Thr Glu Ala Leu Ala Leu Ser<br>                  85                    90                    95 | 288 |
| gat tcc gag ttt act gga aaa ctg tgg tct cta tac ctt gct acc tta<br>Asp Ser Glu Phe Thr Gly Lys Leu Trp Ser Leu Tyr Leu Ala Thr Leu<br>                100                  105                 110 | 336 |
| aaa tct gca cag tac aaa aag cag aat ttt agg cta ggt ata ttt aga<br>Lys Ser Ala Gln Tyr Lys Lys Gln Asn Phe Arg Leu Gly Ile Phe Arg<br>                115                  120                 125 | 384 |
| tca gat tat ttg att gat aag aaa aag ggt act gaa cag att aag caa<br>Ser Asp Tyr Leu Ile Asp Lys Lys Lys Gly Thr Glu Gln Ile Lys Gln<br>130                      135                   140 | 432 |
| gtc gag ttt aat aca gtg tca gtg tca ttt gca ggc ctt agc gag aaa<br>Val Glu Phe Asn Thr Val Ser Val Ser Phe Ala Gly Leu Ser Glu Lys<br>145                      150                   155                 160 | 480 |
| gtt gat aga ttg cac tct tat tta aat agg gca aac aag tac gat cct<br>Val Asp Arg Leu His Ser Tyr Leu Asn Arg Ala Asn Lys Tyr Asp Pro<br>                165                  170                 175 | 528 |
| aaa gga cca att tat aat gat caa aat atg gtc att tct gat tca gga<br>Lys Gly Pro Ile Tyr Asn Asp Gln Asn Met Val Ile Ser Asp Ser Gly<br>                  180                  185                 190 | 576 |
| tac ctt ttg tct aag gca ttg gcc aaa gct gtg gaa tcg tat aag tca<br>Tyr Leu Leu Ser Lys Ala Leu Ala Lys Ala Val Glu Ser Tyr Lys Ser<br>                    195                  200                205 | 624 |
| caa caa agt tct tct aca act agt gat cct att gtc gca ttc att gtg<br>Gln Gln Ser Ser Ser Thr Thr Ser Asp Pro Ile Val Ala Phe Ile Val<br>210                      215                   220 | 672 |
| caa aga aac gag aga aat gtg ttt gat caa aag gtc ttg gaa ttg aat<br>Gln Arg Asn Glu Arg Asn Val Phe Asp Gln Lys Val Leu Glu Leu Asn<br>225                      230                   235                 240 | 720 |
| ctg ttg gaa aaa ttc ggt acc aaa tct gtt agg ttg acg ttt gat gat<br>Leu Leu Glu Lys Phe Gly Thr Lys Ser Val Arg Leu Thr Phe Asp Asp<br>                    245                  250                255 | 768 |
| gtt aac gat aaa ttg ttc att gat gat aaa acg gga aag ctt ttc att<br>Val Asn Asp Lys Leu Phe Ile Asp Asp Lys Thr Gly Lys Leu Phe Ile<br>                    260                  265                270 | 816 |
| agg gac aca gag cag gaa ata gcg gtg gtt tat tac aga acg ggt tac<br>Arg Asp Thr Glu Gln Glu Ile Ala Val Val Tyr Tyr Arg Thr Gly Tyr<br>                275                  280                285 | 864 |
| aca acc act gat tac acg tcc gaa aag gac tgg gag gca aga cta ttc<br>Thr Thr Thr Asp Tyr Thr Ser Glu Lys Asp Trp Glu Ala Arg Leu Phe<br>290                      295                   300 | 912 |
| ctc gaa aaa agt ttc gca ata aag gcc cca gat tta ctc act caa tta<br>Leu Glu Lys Ser Phe Ala Ile Lys Ala Pro Asp Leu Leu Thr Gln Leu<br>305                      310                   315                 320 | 960 |
| tct ggc tcc aag aaa att cag caa ttg tta aca gat gag ggc gta tta<br>Ser Gly Ser Lys Lys Ile Gln Gln Leu Leu Thr Asp Glu Gly Val Leu<br>                    325                  330                335 | 1008 |
| ggt aaa tac atc tcc gat gct gag aaa aag agt agt ttg tta aaa act<br>Gly Lys Tyr Ile Ser Asp Ala Glu Lys Lys Ser Ser Leu Leu Lys Thr | 1056 |

-continued

```
              340                 345                 350
ttt gtc aaa ata tat ccc ttg gat gat acg aag ctt ggc agg gaa ggc      1104
Phe Val Lys Ile Tyr Pro Leu Asp Asp Thr Lys Leu Gly Arg Glu Gly
        355                 360                 365 aag agg ctg gca tta agt gag ccc tct aaa tac gtg tta aaa cca cag      1152
Lys Arg Leu Ala Leu Ser Glu Pro Ser Lys Tyr Val Leu Lys Pro Gln
370                 375                 380 cgg gaa ggt ggc gga aac aat gtt tat aaa gaa aat att cct aat ttt      1200
Arg Glu Gly Gly Gly Asn Asn Val Tyr Lys Glu Asn Ile Pro Asn Phe
385                 390                 395                 400 ttg aaa ggt atc gaa gaa cgt cac tgg gat gca tat att ctc atg gag      1248
Leu Lys Gly Ile Glu Glu Arg His Trp Asp Ala Tyr Ile Leu Met Glu
                405                 410                 415 ttg att gaa cca gag ttg aat gaa aat aat att ata tta cgt gat aac      1296
Leu Ile Glu Pro Glu Leu Asn Glu Asn Asn Ile Ile Leu Arg Asp Asn
            420                 425                 430 aaa tct tac aac gaa cca atc atc agt gaa cta gga att tat ggt tgc      1344
Lys Ser Tyr Asn Glu Pro Ile Ile Ser Glu Leu Gly Ile Tyr Gly Cys
435                 440                 445 gtt cta ttt aac gac gag caa gtt tta tcg aac gaa ttt agt ggc tca      1392
Val Leu Phe Asn Asp Glu Gln Val Leu Ser Asn Glu Phe Ser Gly Ser
    450                 455                 460 tta cta aga tcc aaa ttt aat act tca aat gaa ggt gga gtg gcg gca      1440
Leu Leu Arg Ser Lys Phe Asn Thr Ser Asn Glu Gly Gly Val Ala Ala
465                 470                 475                 480 gga ttc gga tgt ttg gac agt att att ctt tac tag gtgtacatgt           1486
Gly Phe Gly Cys Leu Asp Ser Ile Ile Leu Tyr
                485                 490 actatacaca tagatgctag gaagatgatg ctagaacttg attaacaatt agttaaggaa    1546
tatataatca cacttctaca taaatttgct gttttaggct cattccttct ttctttcacc    1606
ctttagtagc gaagtacacc atttagctgc accaacagtg ttgctagata tggtgactat    1666
tgtgaagaag ggtattaact ctagtagacc ggcagacata ccgaaacata tgaaacttgc    1726
gtaatgctcg tactgaaaat ctttggcctg tttcttactg aatccctttta gtaaaaagta   1786
cctctgcaaa taggtaaagg ttcttttttgg ggccattagt tgatttgcca agattggtcc   1846
tacaatagga attagcgaca gtaatgttag tgaagtaaaa ttggagactt taaaaaacat    1906
tctgaatagt aatctgggaa tcttaaaaat ccgacttccc tttattgtgt tgaaatttct    1966
caccgcatca ggttcatcga ttttctatg tggcttttgt ggtttaggca ataccttcac     2026
ctcgtttaga aattcatctt ggtcttgcaa caccaaagat atatcaaata tctgattcgt    2086
aatatgggtc aggaccagtg ttctacaaac aaaggcagtc aagacattcg tttgtaaaat    2146
ccattgaata tgaaccagta tcacaccaag aggccctaat aacagtatgg cccatgtcac    2206
taaaagcggt acaagtgtga cataaaaagag accagcaata gtgacaaaaa tcagggcata   2266
gcaaaccgca aacagtaaaa tatgcttcca ataaacagga ttcgtcagca cttcataaaa    2326
cccctacggt taacaaataa aaattaaata tgttagtcat aaaacaagtc atatcaatgc    2386
aaacaaaaat catgtgtactta ctaagaatgg gtagataaat gctcttgagt tgaaaatttc   2446
tttaatgaag ttttttctaa                                                 2466
```

<210> SEQ ID NO 2
<211> LENGTH: 491
<212> TYPE: PRT
<213> ORGANISM: Saccharomyces cerevisiae

<400> SEQUENCE: 2

-continued

```
Met Ala His Tyr Pro Pro Ser Lys Asp Gln Leu Asn Glu Leu Ile Gln
1               5                   10                  15

Glu Val Asn Gln Trp Ala Ile Thr Asn Gly Leu Ser Met Tyr Pro Pro
            20                  25                  30

Lys Phe Glu Glu Asn Pro Ser Asn Ala Ser Val Ser Pro Val Thr Ile
        35                  40                  45

Tyr Pro Thr Pro Ile Pro Arg Lys Cys Phe Asp Glu Ala Val Gln Ile
    50                  55                  60

Gln Pro Val Phe Asn Glu Leu Tyr Ala Arg Ile Thr Gln Asp Met Ala
65                  70                  75                  80

Gln Pro Asp Ser Tyr Leu His Lys Thr Thr Glu Ala Leu Ala Leu Ser
                85                  90                  95

Asp Ser Glu Phe Thr Gly Lys Leu Trp Ser Leu Tyr Leu Ala Thr Leu
            100                 105                 110

Lys Ser Ala Gln Tyr Lys Lys Gln Asn Phe Arg Leu Gly Ile Phe Arg
        115                 120                 125

Ser Asp Tyr Leu Ile Asp Lys Lys Gly Thr Glu Gln Ile Lys Gln
130                 135                 140

Val Glu Phe Asn Thr Val Ser Val Ser Phe Ala Gly Leu Ser Glu Lys
145                 150                 155                 160

Val Asp Arg Leu His Ser Tyr Leu Asn Arg Ala Asn Lys Tyr Asp Pro
                165                 170                 175

Lys Gly Pro Ile Tyr Asn Asp Gln Asn Met Val Ile Ser Asp Ser Gly
            180                 185                 190

Tyr Leu Leu Ser Lys Ala Leu Ala Lys Ala Val Glu Ser Tyr Lys Ser
        195                 200                 205

Gln Gln Ser Ser Ser Thr Thr Ser Asp Pro Ile Val Ala Phe Ile Val
        210                 215                 220

Gln Arg Asn Glu Arg Asn Val Phe Asp Gln Lys Val Leu Glu Leu Asn
225                 230                 235                 240

Leu Leu Glu Lys Phe Gly Thr Lys Ser Val Arg Leu Thr Phe Asp Asp
                245                 250                 255

Val Asn Asp Lys Leu Phe Ile Asp Asp Lys Thr Gly Lys Leu Phe Ile
            260                 265                 270

Arg Asp Thr Glu Gln Glu Ile Ala Val Val Tyr Arg Thr Gly Tyr
        275                 280                 285

Thr Thr Thr Asp Tyr Thr Ser Glu Lys Asp Trp Glu Ala Arg Leu Phe
    290                 295                 300

Leu Glu Lys Ser Phe Ala Ile Lys Ala Pro Asp Leu Leu Thr Gln Leu
305                 310                 315                 320

Ser Gly Ser Lys Lys Ile Gln Gln Leu Leu Thr Asp Glu Gly Val Leu
                325                 330                 335

Gly Lys Tyr Ile Ser Asp Ala Lys Lys Ser Ser Leu Leu Lys Thr
            340                 345                 350

Phe Val Lys Ile Tyr Pro Leu Asp Asp Thr Lys Leu Gly Arg Glu Gly
        355                 360                 365

Lys Arg Leu Ala Leu Ser Glu Pro Ser Lys Tyr Val Leu Lys Pro Gln
    370                 375                 380

Arg Glu Gly Gly Gly Asn Asn Val Tyr Lys Glu Asn Ile Pro Asn Phe
385                 390                 395                 400

Leu Lys Gly Ile Glu Glu Arg His Trp Asp Ala Tyr Ile Leu Met Glu
                405                 410                 415
```

Leu Ile Glu Pro Glu Leu Asn Glu Asn Asn Ile Ile Leu Arg Asp Asn
                420                 425                 430

Lys Ser Tyr Asn Glu Pro Ile Ile Ser Glu Leu Gly Ile Tyr Gly Cys
            435                 440                 445

Val Leu Phe Asn Asp Glu Gln Val Leu Ser Asn Glu Phe Ser Gly Ser
        450                 455                 460

Leu Leu Arg Ser Lys Phe Asn Thr Ser Asn Glu Gly Gly Val Ala Ala
465                 470                 475                 480

Gly Phe Gly Cys Leu Asp Ser Ile Ile Leu Tyr
                485                 490

<210> SEQ ID NO 3
<211> LENGTH: 25
<212> TYPE: DNA
<213> ORGANISM: Artificial Sequence
<220> FEATURE:
<223> OTHER INFORMATION: Synthetic DNA

<400> SEQUENCE: 3
cataaaacaa ctgaagcgtt agctc                                      25

<210> SEQ ID NO 4
<211> LENGTH: 25
<212> TYPE: DNA
<213> ORGANISM: Artificial Sequence
<220> FEATURE:
<223> OTHER INFORMATION: Synthetic DNA

<400> SEQUENCE: 4
caggccaaag attttcagta cgagc                                      25

<210> SEQ ID NO 5
<211> LENGTH: 28
<212> TYPE: DNA
<213> ORGANISM: Artificial Sequence
<220> FEATURE:
<223> OTHER INFORMATION: Synthetic DNA

<400> SEQUENCE: 5
ccacagcggg aagatggcgg aaacaatg                                   28

<210> SEQ ID NO 6
<211> LENGTH: 28
<212> TYPE: DNA
<213> ORGANISM: Artificial Sequence
<220> FEATURE:
<223> OTHER INFORMATION: Synthetic DNA

<400> SEQUENCE: 6
cattgtttcc gccatcttcc cgctgtgg                                   28

<210> SEQ ID NO 7
<211> LENGTH: 25
<212> TYPE: DNA
<213> ORGANISM: Artificial Sequence
<220> FEATURE:
<223> OTHER INFORMATION: Synthetic DNA

<400> SEQUENCE: 7
ctaatatgga tgtcggcaac ccaag                                      25

<210> SEQ ID NO 8
<211> LENGTH: 24
<212> TYPE: DNA

-continued

```
<213> ORGANISM: Artificial Sequence
<220> FEATURE:
<223> OTHER INFORMATION: Synthetic DNA

<400> SEQUENCE: 8
ccacagcttt ggccaatgcc ttag                                   24

<210> SEQ ID NO 9
<211> LENGTH: 31
<212> TYPE: DNA
<213> ORGANISM: Artificial Sequence
<220> FEATURE:
<223> OTHER INFORMATION: Synthetic DNA

<400> SEQUENCE: 9
cggtgtcacc agtaattatc tatccaaccc c                           31

<210> SEQ ID NO 10
<211> LENGTH: 31
<212> TYPE: DNA
<213> ORGANISM: Artificial Sequence
<220> FEATURE:
<223> OTHER INFORMATION: Synthetic DNA

<400> SEQUENCE: 10
ggggttggat agataattac tggtgacacc g                           31
```